United States Patent
Song et al.

(10) Patent No.: US 12,039,720 B2
(45) Date of Patent: Jul. 16, 2024

(54) AUTOMATIC ESTIMATION OF TUMOR CELLULARITY USING A DPI AI PLATFORM

(71) Applicants: Sony Group Corporation, Tokyo (JP); Sony Corporation of America, New York, NY (US)

(72) Inventors: Bi Song, San Jose, CA (US); Ko-Kai Albert Huang, Cupertino, CA (US); Ming-Chang Liu, San Jose, CA (US)

(73) Assignees: SONY GROUP CORPORATION, Tokyo (JP); SONY CORPORATION OF AMERICA, New York, NY (US)

( * ) Notice: Subject to any disclaimer, the term of this patent is extended or adjusted under 35 U.S.C. 154(b) by 539 days.

(21) Appl. No.: 17/348,436

(22) Filed: Jun. 15, 2021

(65) Prior Publication Data
US 2022/0398719 A1   Dec. 15, 2022

(51) Int. Cl.
*G06T 7/00* (2017.01)
*G06N 3/045* (2023.01)
(Continued)

(52) U.S. Cl.
CPC ............ *G06T 7/0012* (2013.01); *G06N 3/045* (2023.01); *G06N 3/08* (2013.01); *G16H 10/40* (2018.01);
(Continued)

(58) Field of Classification Search
CPC ......... G06T 7/0012; G06T 2207/10056; G06T 2207/20081; G06T 2207/20084; G06T 2207/30024; G06T 2207/30096; G06N 3/045; G06N 3/08; G16H 10/40; G16H 30/40; G16H 50/20; G16H 70/60;
(Continued)

(56) References Cited

U.S. PATENT DOCUMENTS

2021/0050094 A1*   2/2021   Orringer ................ G01N 21/65

FOREIGN PATENT DOCUMENTS

| WO | WO2019108695 A1 | 6/2019 |
| WO | WO2020014477 A1 | 1/2020 |

OTHER PUBLICATIONS

Dov David et al: "Machine Learning for Healthcare Thyroid Cancer Malignancy Prediction From Whole Slide Cytopathology Images", Proceedings of Machine Learning Research, Mar. 29, 2019 (Mar. 29, 2019) XP055952237, Retrieved from the Internet: URL:https://proceedings.mlr.press/v106/dov19a.
(Continued)

*Primary Examiner* — Christopher M Brandt
(74) *Attorney, Agent, or Firm* — Trellis IP Law Group, PC

(57) ABSTRACT

A method for automatically estimating cellularity in a digital pathology slide image includes: extracting patches of interest from the digital pathology slide image; operating on each patch using a trained first deep convolutional neural network (DCNN) to classify that patch as either normal, having an estimated cellularity of 0%, or suspect, having a cellularity roughly estimated to be greater than 0%; operating on each suspect patch using a second DCNN, trained using a deep ordinal regression model, to determine an estimated cellularity score for that suspect patch; and combining the estimated cellularity scores of the patches of interest to provide an estimated cellularity for the digital pathology slide image at a patch-by-patch level.

20 Claims, 7 Drawing Sheets

(51) Int. Cl.
- *G06N 3/08* (2023.01)
- *G16H 10/40* (2018.01)
- *G16H 30/40* (2018.01)
- *G16H 50/20* (2018.01)
- *G16H 70/60* (2018.01)

(52) U.S. Cl.
CPC ............ *G16H 30/40* (2018.01); *G16H 50/20* (2018.01); *G16H 70/60* (2018.01); *G06T 2207/10056* (2013.01); *G06T 2207/20081* (2013.01); *G06T 2207/20084* (2013.01); *G06T 2207/30024* (2013.01); *G06T 2207/30096* (2013.01)

(58) Field of Classification Search
CPC .. G06V 10/7753; G06V 10/82; G06V 20/698; G06V 20/69
See application file for complete search history.

(56) References Cited

OTHER PUBLICATIONS

Rakhlin Alexander et al: "Breast Tumor Cellularity Assessment Using Deep Neural Networks", 2019 IEEE/CVF International Conference on Computer Vision Workshop (ICCVW), IEEE, Oct. 27, 2019 (Oct. 27, 2019), pp. 371-380, XP033732800, DOI: 10.1109/ICCVW.2019.00048.

Axel Berg et al: "Deep Ordinal Regression with Label Diversity", arxiv.org, Cornell University Library, 201 Olin Library Cornell University Ithaca, NY 14853, Jun. 29, 2020 (Jun. 29, 2020), XP08193220, DOI: 10.1109/ICPR48806.2021.9412608.

Xiao Lichao et al: "Censoring-Aware Deep Ordinal Regression for Survival Prediction from Pathological Images" Sep. 29, 2020 (Sep. 29, 2020), arxiv,org, Cornell University Library, 201 Olin Library Cornell University Ithaca, NY, 145853, pp. 449-458, XP047564083.

Niu Zhenxing et al: "Ordinal Regression with Multiple Output CNN for Age Estimation" , 2016 IEEE Conference on Computer Vision and Pattern Recognition (CVPR), IEEE, Jun. 27, 2016 (Jun. 27, 2016), pp. 4920-4928, XP033021685, DOI: 10.1109/CVPR.2016.532.

"Breast Tumor Cellularity Assessment using Deep Neural Networks" https://openaccess.thecvf.com/content_ICCVW_2019/html/VRMI/Rakhlin_Breast_Tumor_Cellularity_Assessment_Using_Deep_Neural_Networks_ICCVW_2019_paper.html.

* cited by examiner

AUTOMATIC ESTIMATION OF TUMOR CELLULARITY USING A DPI AI PLATFORM

BACKGROUND

In the field of cancer treatment in general, neoadjuvant therapy (NAT), the administration of therapeutic agents prior to surgery, can be very successful in downstaging tumors, making it feasible to conduct tissue-conserving surgery rather than more drastic surgical options. In breast cancer, for example, which is one of the most common cancers in women, NAT may significantly reduce the amount of normal breast tissue that would otherwise be removed during surgery.

After NAT is performed, the amount of cancerous tissue that remains—the residual cancer burden or residual tumor burden—is an indicator of the effectiveness of NAT in that individual case, and it has been found to be a useful prognostic for long term survival. The "gold standard" for assessing residual tumor is pathological examination of tissue sections to assess tumor cellularity, defined as the proportion (usually expressed as a percentage) of the cells visible in the tissue sections that are cancerous rather than normal.

In current clinical practice, tumor cellularity (which may be referred to elsewhere in this disclosure simply as "cellularity") is estimated manually, by a pathologist examining a patient's tissue sample after it has been sectioned and stained (typically with hematoxylin and eosin, or H&E). FIG. 1 schematically illustrates parts of the process, where a slice of suspected cancer cell-containing tissue 110, stained with H&E, is removed from surrounding normal tissue 120, divided into sections (A1 through A5 in the example shown), each of which is then mounted onto a corresponding slide (such as 141 through 145), and viewed through a microscope.

The pathologist can then study one or more regions of the tissue section on the slide, comparing the proportion of residual tumor bed area containing cancer with standard cellularity references, such as set 200 shown in FIG. 2. Set 200 includes, on the left of the figure, images of microscope fields that would be observed for tissue sections with cellularity values ranging from 1% through 30%, including a subset that shows grouped patterns of stained cell distributions, as seen in fields 211 through 215, and another that shows scattered patterns of stained cell distributions, as seen in fields 221 through 225. Set 200 also includes, on the right, images of microscope fields that would be observed for tissue sections with higher cellularity values ranging from 40% through 95%. As the distinction between the two types of distribution patterns is less meaningful in these higher ranges, only one reference image is provided for each cellularity value, as seen in fields 231 through 237.

The pathologist can then compare the appearance of each viewed tissue section with the reference set to come up with an estimate of cellularity, in terms of the percentage of area occupied by tumor cells relative to normal cells in that section. In the FIG. 1 case, that means the pathologist would generate five "local" cellularity values, one for each of slides 141 through 145, and could then calculate an average or overall cellularity for the whole tissue sample 110.

Such manual estimations of cellularity, each involving a series of visual comparisons or matching tasks, are time consuming. Moreover, the quality and reliability of estimations made manually by different people—different raters—is, of course, subject to inter-rater variability, which can degrade the prognostic power of the estimations, in NAT trials and in regular patient care.

There is, therefore, a need for time-efficient methods of estimating cellularity that are less manual, and less dependent on the individual pathologist's skill and consistency. Such methods would ideally take advantage of technical advancements in digital pathology to save time, reduce the influence of human error, increase inter-observer agreement, and thus improve reproducibility and diagnosis accuracy.

SUMMARY

Embodiments generally relate to systems and methods for automatically estimating cellularity in digital pathology slide images. In one embodiment, a method comprises: extracting patches of interest from the digital pathology slide image; operating on each of the extracted patches using a trained first deep convolutional neural network (DCNN) to classify that patch as either normal, having an estimated cellularity of 0%, or suspect, having a cellularity roughly estimated to be greater than 0%; operating on each of the suspect patches using a second DCNN, trained using a deep ordinal regression model, to determine an estimated cellularity score for that suspect patch; and combining the estimated cellularity scores of the patches of interest to provide an estimated cellularity for the digital pathology slide image at a patch-by-patch level.

In another embodiment, a method of training first and second deep convolutional neural networks to automatically estimate cellularity of digital pathology slide images comprises: training the first deep convolutional neural network (DCNN) to classify each of a first plurality of training digital pathology images input to the first DCNN as either normal, having an estimated cellularity of 0%, or suspect, having a roughly estimated cellularity greater than 0%; and training the second DCNN to estimate a cellularity score of each of a second plurality of training digital pathology images, using an ordinal regression model.

In yet another embodiment, an apparatus for automatically estimating cellularity in a digital pathology slide image comprises: one or more processors; and logic encoded in one or more non-transitory media for execution by the one or more processors. When the logic is executed, it is operable to: extract patches of interest from the digital pathology slide image; operate on each of the extracted patches using a trained first deep convolutional neural network (DCNN) to classify that patch as either normal, having an estimated cellularity of 0%, or suspect, having a cellularity roughly estimated to be greater than 0%; operate on each of the suspect patches using a second DCNN, trained using a deep ordinal regression model, to determine an estimated cellularity score for that suspect patch; and combine the estimated cellularity scores of the patches of interest to provide an estimated cellularity for the digital pathology slide image at a patch-by-patch level.

A further understanding of the nature and the advantages of particular embodiments disclosed herein may be realized by reference to the remaining portions of the specification and the attached drawings.

DETAILED DESCRIPTION OF EMBODIMENTS

Embodiments described herein are directed to the automatic estimation of cellularity in digital pathology slide images. The present invention uses a DPI AI platform to perform the estimation, trained and operational in accordance with the methods and systems described below.

Figure 3:
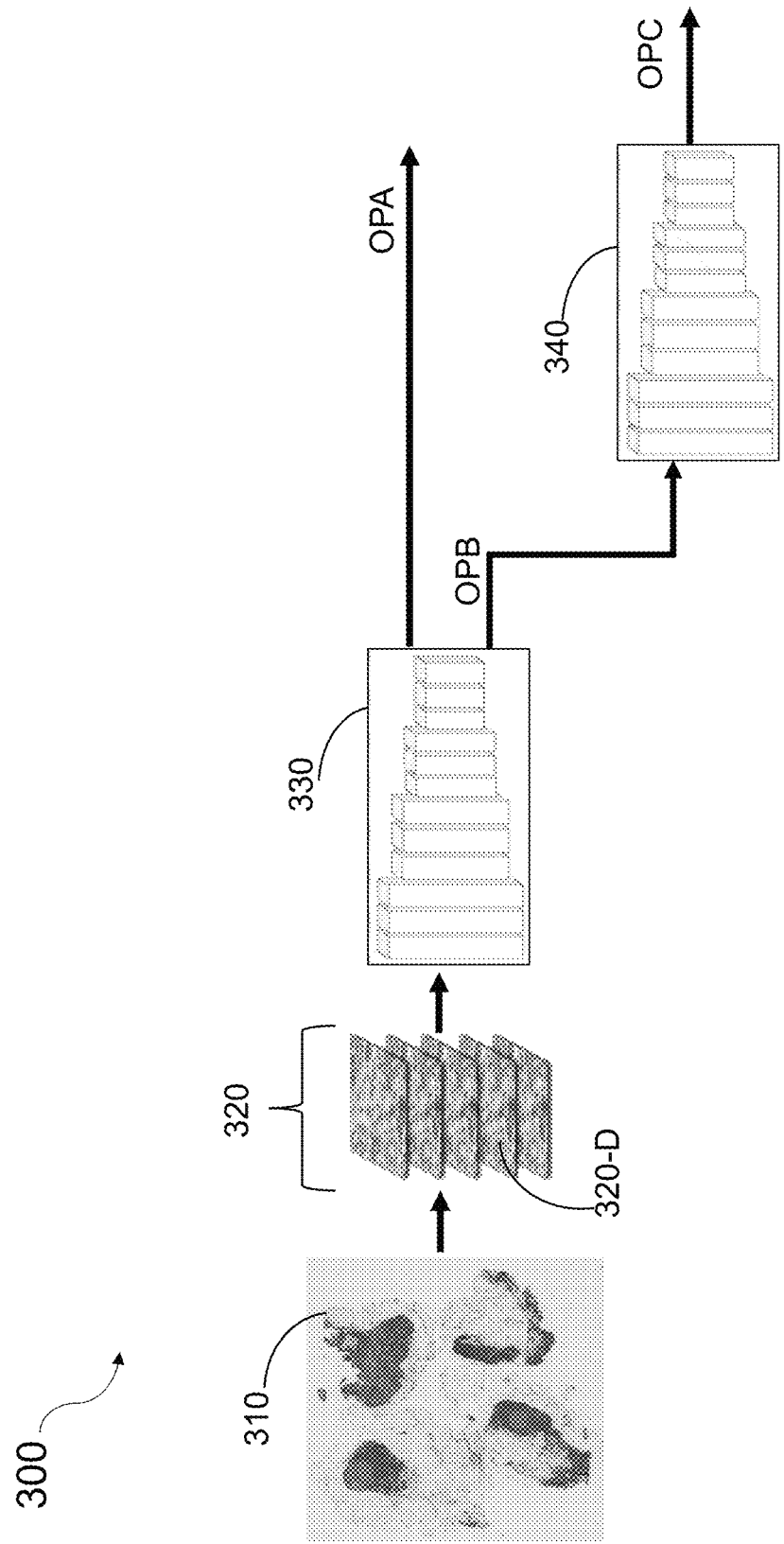
FIG. 3 schematically illustrates a system for cellularity estimation according to some embodiments of the present invention.

FIG. 3 schematically illustrates a system 300 for cellularity estimation according to some embodiments of the present invention. System input 310 is a digital pathology slide image of the stained tissue section of interest. The first action performed by system 300 is the extraction of a set 320 of patches from 310, to keep the data load to be processed in each extracted patch (such as 320-D) of the set of patches 320 manageably low. In some cases, the extraction may optionally involve a background removal step, to exclude regions of the patch exhibiting no suggestion of staining.

Figure 1:
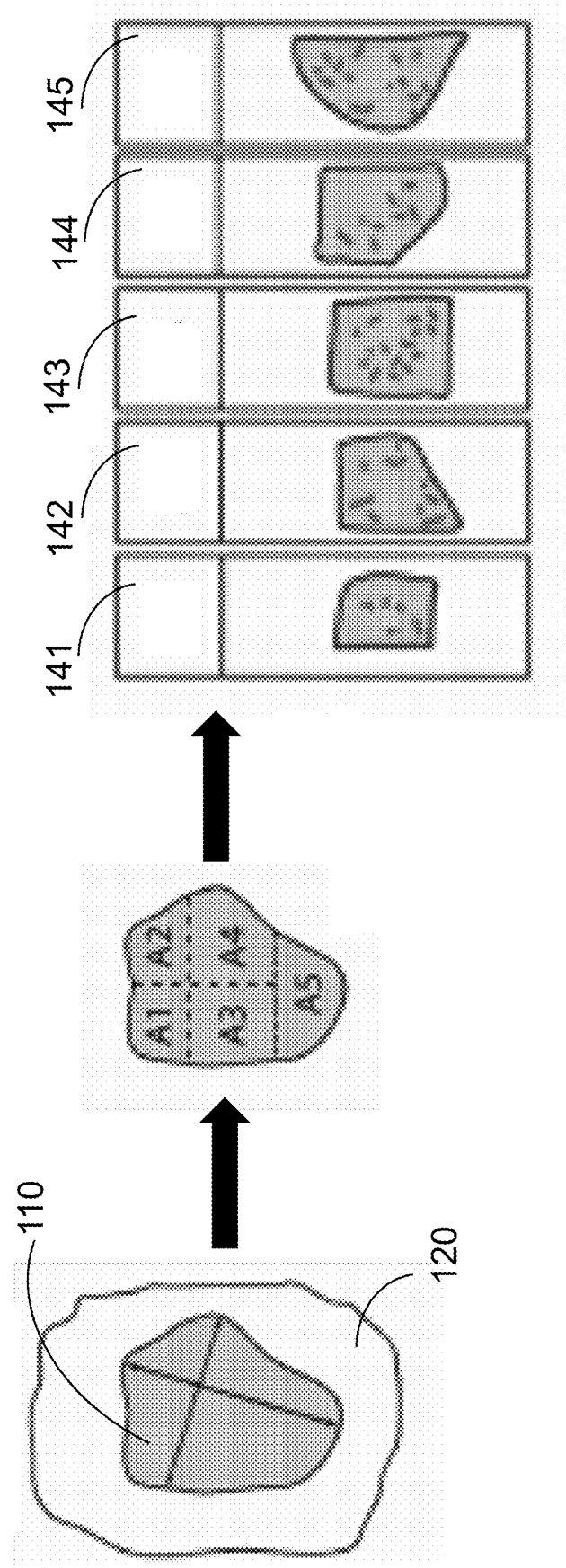
FIG. 1 illustrates a sequence of steps involved in prior art manual estimations of cellularity.
Figure 2:
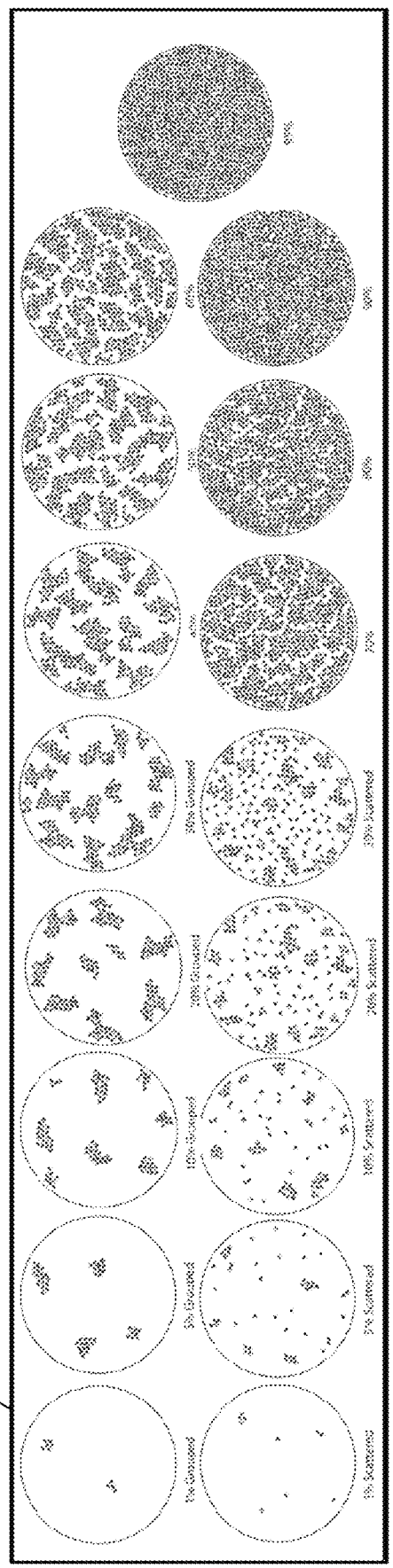
FIG. 2 illustrates a set of reference fields used in prior art manual estimations of cellularity.

Each of the extracted patches may be considered as roughly corresponding to a microscope field image of tissue on a slide (like slide 141, for example) in prior art methods such as that of FIG. 1.

The next action is feeding one patch at a time into deep convolutional neural network (DCNN) 330. DCNN 330 has been previously trained using relatively conventional AI image classification methods to operate on any input patch to classify it as either normal, meaning that it has an estimated cellularity of 0%, or suspect, meaning that it has a cellularity that is estimated, by a relatively rough estimation process, to be greater than 0%. When trained DCNN 330 is subsequently used in system 300 and receives an input patch, it will produce an output at OPA if it determines the patch is normal but will send the patch on though output OPB if it determines the patch is suspect. It has been found experimentally that while a trained DCNN such as DCNN 330 can be relied on to not mistakenly classify patches of greater than 0% cellularity as normal, it may mistakenly classify a few normal patches as being suspect, meaning that a small fraction of patches in stream OPB will actually be also be of 0% cellularity i.e. normal. Hence, the term "suspect" is a more accurate term than "cancerous" to describe the OPB patches.

In the routine operation of system 300, the OPB stream feeds the suspect patches, one at a time, into DCNN 340, which has been previously trained using a deep ordinal regression model (which will be described in more detail below) to operate on any input patch to estimate a corresponding cellularity score in the range of 0% to 100%. When trained DCNN 340 is subsequently used in system 300 and receives a stream of suspect input patches through OPB, it will estimate a cellularity score for each patch, and produce an output stream at OPC with a corresponding estimated cellularity score for each patch.

Cellularity scores can thus be provided for all the input patches, and a detailed analysis across the entire whole slide image 310 performed.

Figure 4:
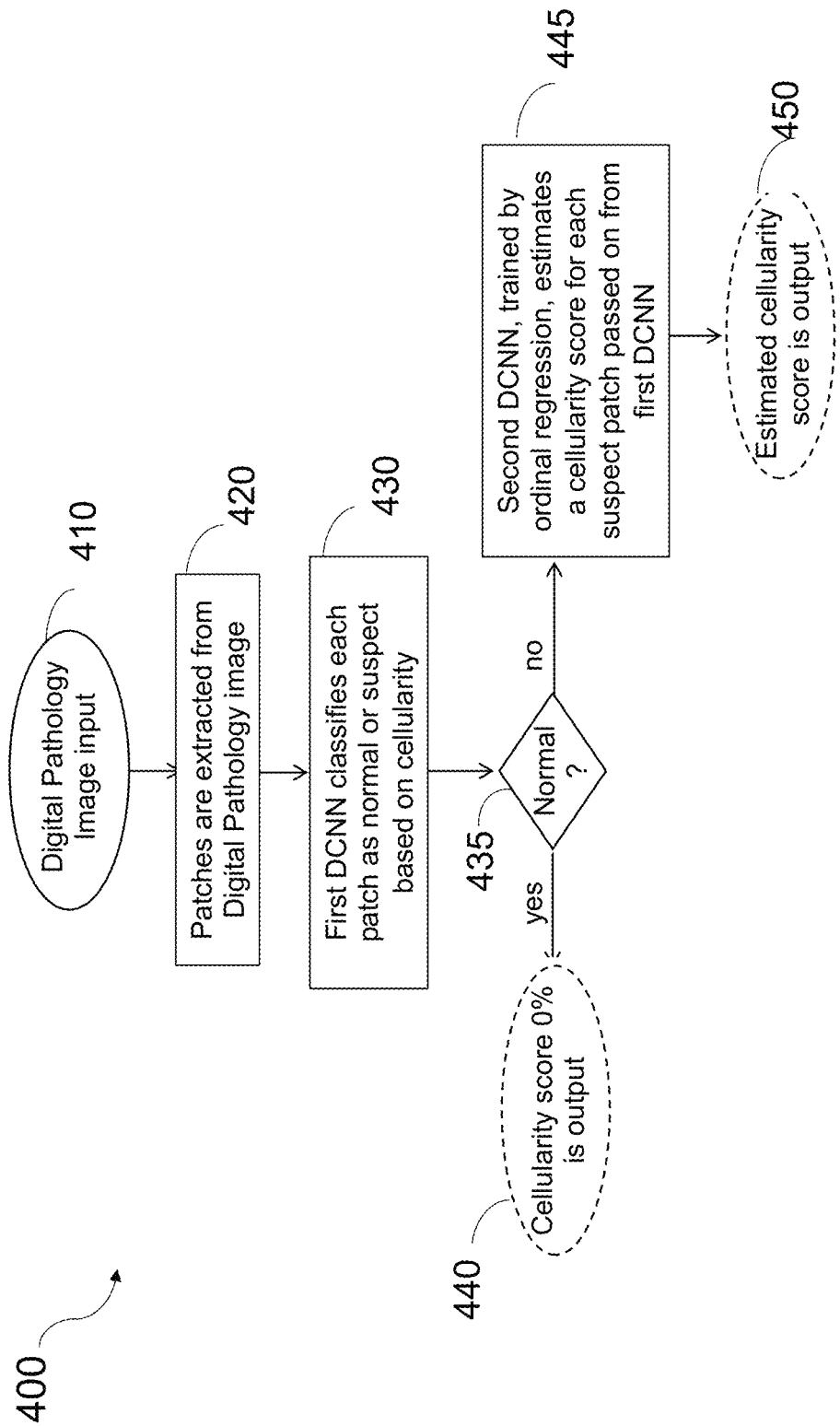
FIG. 4 is a flowchart illustrating a method for cellularity estimation according to some embodiments of the present invention.

FIG. 4 is a flowchart of steps in a method 400 for cellularity estimation according to some embodiments of the present invention. At step 410, a Digital Pathology Image, such as that shown as 310 in FIG. 3, is input. At step 420, a patch extraction process is carried out on 310, to optionally remove regions of no interest, and to divide the remaining region or regions into patches (like patch 320D) of manageable data content.

At step 430, a trained DCNN such as that shown as 330 in FIG. 3 operates on each patch in turn to classify it as either normal, meaning that its cellularity is estimated to be 0%, or suspect, meaning that its cellularity is roughly estimated to be greater than 0%. Step 435 checks the classification of each patch, and for each one classified as normal, provides a corresponding indication of normality—a cellularity core of 0%—as an output at step 440. As noted above in discussing FIG. 3, this DCNN is assumed to have been previously trained using conventional AI image classification methods, which have been found to be quite successful in the role of not misclassifying suspect patches as normal. However, they typically have an appreciable failure rate in the reverse direction, meaning that a significant fraction—maybe 5%—of patches they classify as suspect are actually of 0% cellularity and should ideally have been classified as normal.

When step 435 finds a patch classified as suspect, but as noted above has a small chance of actually being normal, that patch is operated on by a second DCNN which, unlike the DCNN used at step 430, has been trained by an ordinal regression model technique, which does not involve separately assigning different patches into different categories on the basis of apparent cellularity. Instead, this second DCNN operates, at step 445, to estimate a specific cellularity score for each suspect patch, and that cellularity score is provided as an output at step 450.

Figure 5:
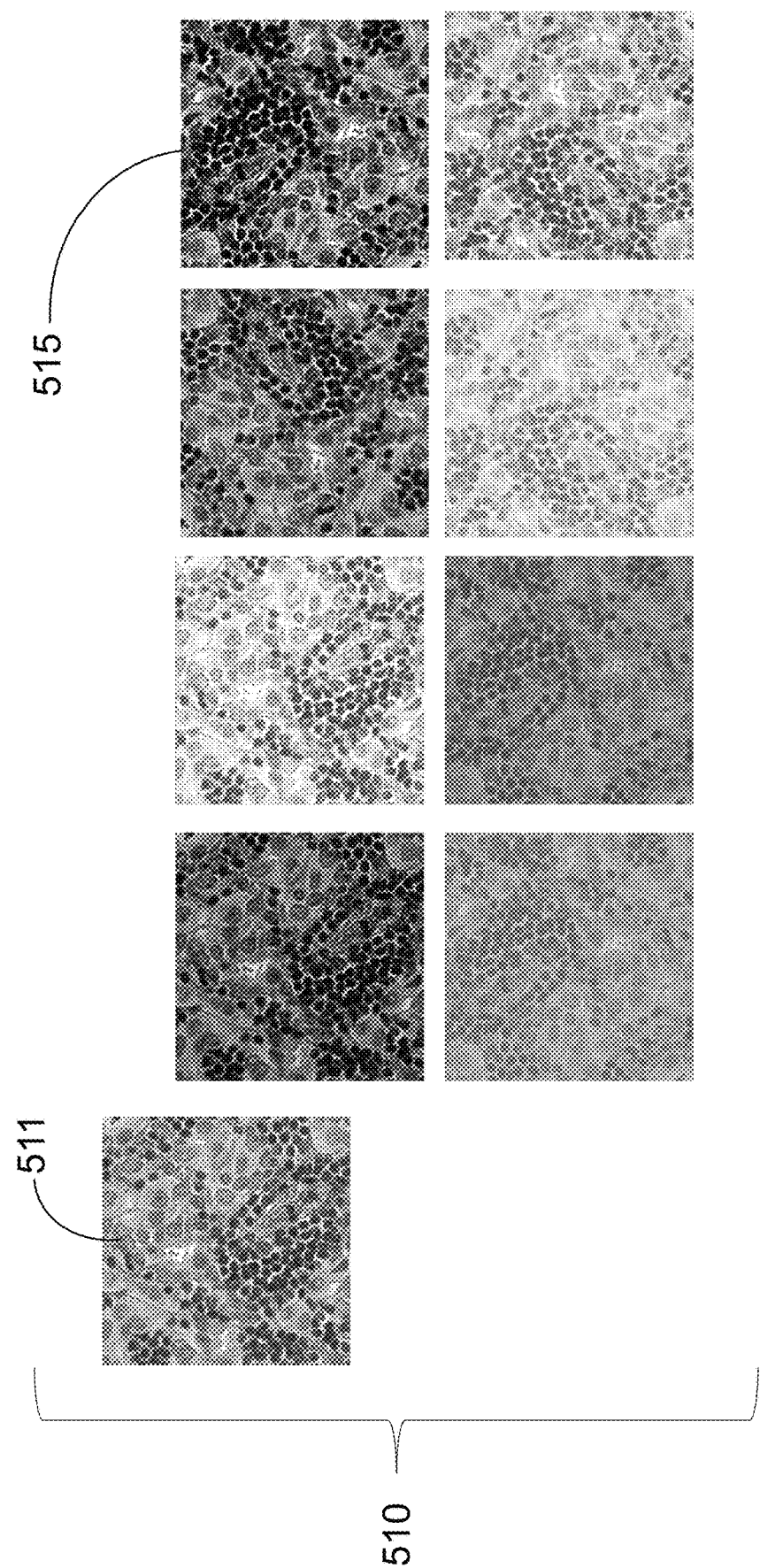
FIG. 5 illustrates an augmented set of training images that may be used in some embodiments of the present invention.

The training of the two DCNNs used in embodiments of the present invention is done with the use of training DPI images, of similar size and image quality as those of image patches the DCNNs will later be expected to process. FIG. 5 shows an example of one such training image 511, as captured from a stained tissue section (normally from an organ or organs of interest) whose ground truth cellularity has been assessed by some credible means, usually manually by one or more expert pathologists. Obtaining a sufficient number of such images to provide good training is made easier by data augmentation, a technique well-known in the field of machine learning for processing "natural" images, but which is adapted in the present invention to DPI images. In the case of FIG. 5, initial image 511 acts as a "seed" image for a whole batch 510 of images, which are derived from 511 by simple image manipulations such as color perturbations, rotations, flips, etc. Image 515, for example, is derived from 511 by a 180° rotation and changes in brightness and contrast. In some cases, blurring or other types of image degradation or enhancement may be employed in addition to or in combination with such adjustments. By such means, training image sets may be generated and used as training inputs, covering the entire cellularity range expected to be encountered with without requiring each training image to be obtained from a unique tissue section image.

In some embodiments, different sets of training images are used for DCNNs to be used for classifying images and normal or suspect (meaning DCNNs serving the function of DCNN 330) than for DCNNs to be used for cellularity score estimations (meaning DCNNs serving the function of DCNN 340), maybe with a larger proportion of images of 0% cellularity in the former set than in the latter. In other embodiments, the same set of training images may be used for both types of DCNN.

In training the first DCNN of a system of the present invention, like DCNN 330 in system 300, a relatively straightforward iterative process is involved, of a type well known to one of skill in the art. As the goal of this DCNN is simply to classify images as either normal (0% cellularity) or suspect (>0% cellularity), an initial classification of each image of the training set can be compared with a rough classification based on ground truth for that image—or the seed image from which that image was derived—and then weighting and connectivity parameters of the internal DCNN backbone iteratively adjusted until an acceptable matching rate is achieved.

Figure 6:
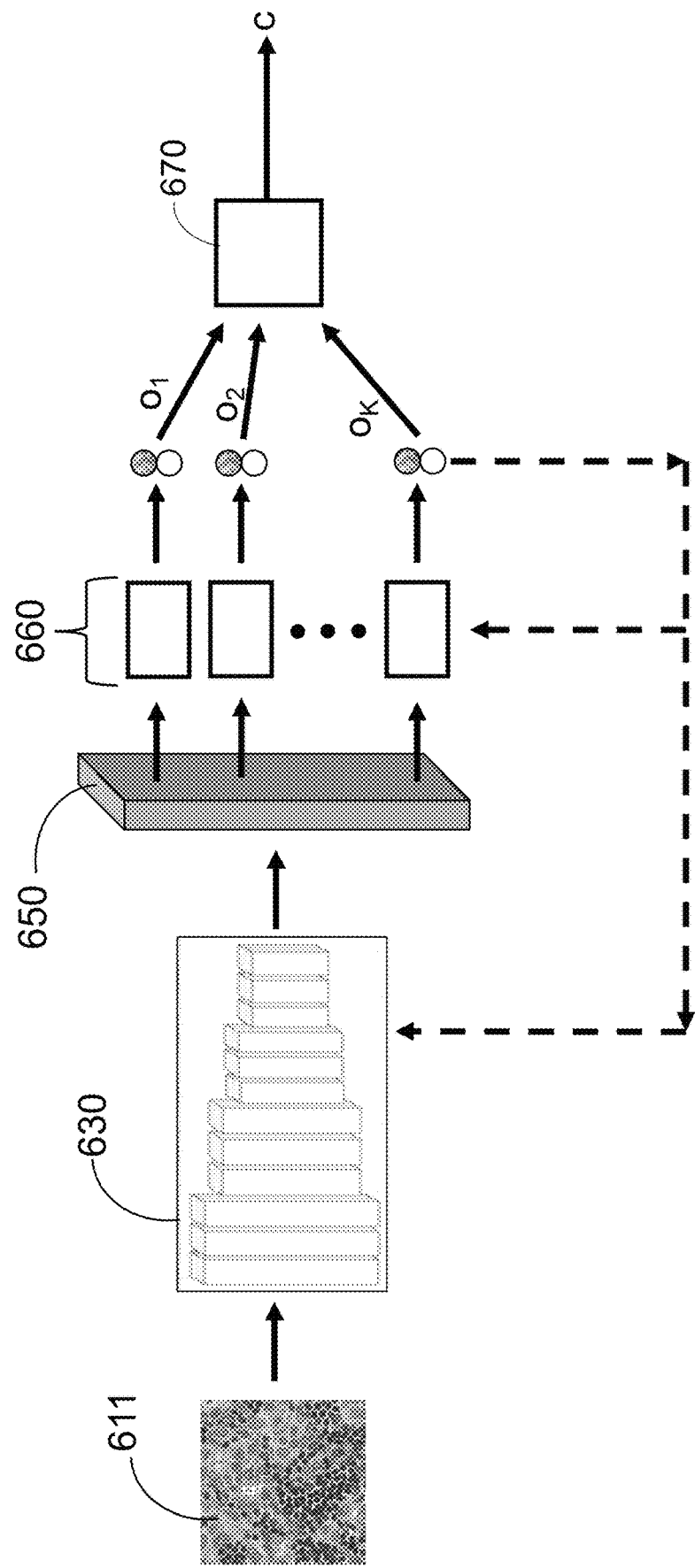
FIG. 6 schematically illustrates an ordinal regression method used in some embodiments of the present invention.

In training the second DCNN of a system of the present invention, like DCNN 340 in FIG. 3, a very different approach is taken. Instead of a classification approach that sorts the images out into different categories based on an assessment of whether their cellularity falls into one range or another, an ordinal regression technique is used which involves intermediate steps where a series of ordinal values are determined and then combined, to provide an estimate of a particular cellularity score for each image. An overview of how this is carried out is presented in FIG. 6.

Consider a digital pathology image 611 fed into the DCNN model 630. Image 611 is representative of images that the first DCNN in a system of the present invention (like 330 in system 300) might have classified as suspect. DCNN model 630 operates on image 611 in a relatively conventional way to extract image features 650 from the input image. Such feature extraction methods are well known in processing natural images, but in the present invention are applied to the processing of DPI images.

Then the network branches out into a stack of K output layers (660), where each output layer (or binary classifier) contains 2 neurons and corresponds to a binary classification task. The k-th task is to predict whether the cellularity of the input image is larger than the rank Ck. Each binary classifier in stack 660 outputs a "1" or a "0" depending on the comparison. For example, one classifier might output a "1" if it predicts the cellularity of input image 611 is above 5%, while another might do so if it predicts the cellularity of input image 611 is above 10%, and so on. The binary outputs (ok for the k-th classifier) generated by the output layers 660 are then "fused" or mathematically combined at fusing element 670 which weights the outputs of different classifiers differently, to provide a fused cellularity score "c". When this cellularity score is compared with a ground truth cellularity score for input image 611, an iterative process can be carried out (indicated by the dashed lines in the figure) to adjust parameters in the output layer 660 and in the DCNN model 630 to optimize the loss function of the binary classifiers. Those parameters and weights are then fixed, and the DCNN considered to be trained, with the fused score being the desired output.

Figure 7:
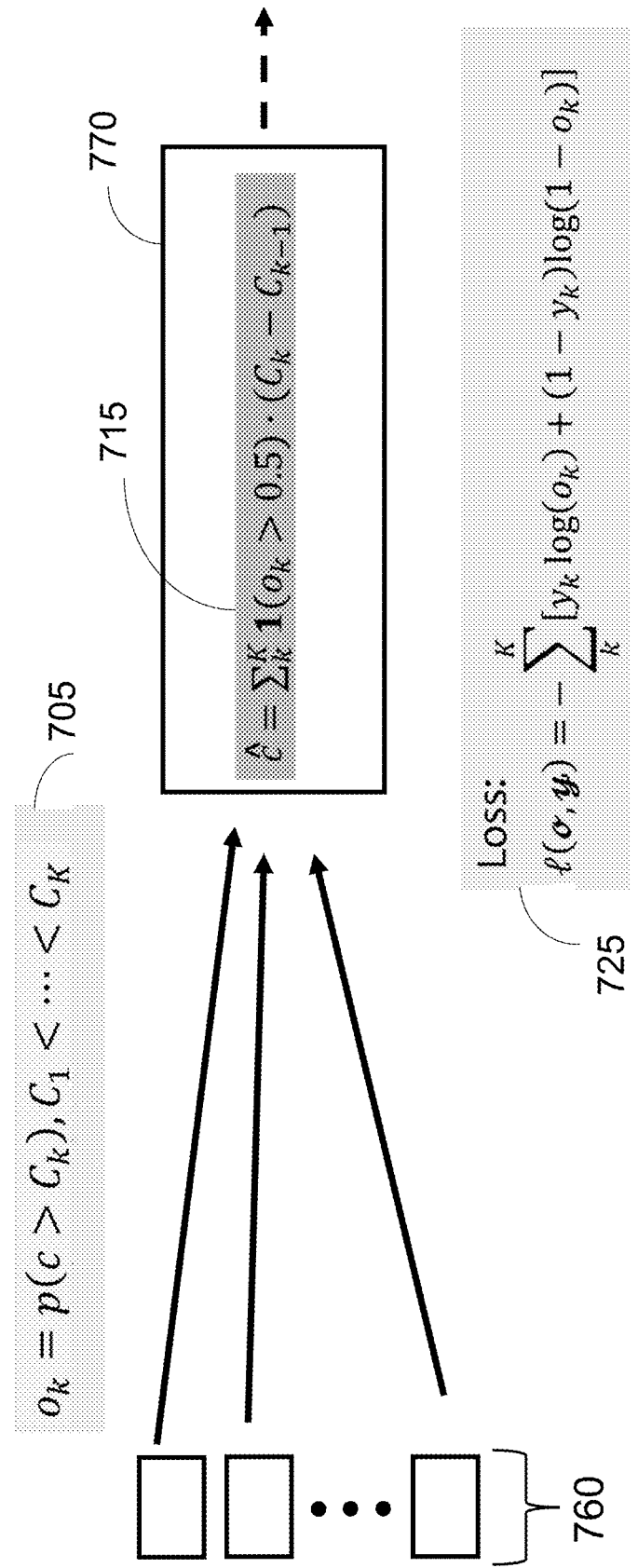
FIG. 7 illustrates mathematical details of an ordinal regression method used in some embodiments of the present invention.

Some of the mathematical details involved in the operation of the binary classifiers, the fusing element, and the loss function in one embodiment of the present invention are shown in FIG. 7. Equation 705 represents the output of the kth binary classifier in output layers 760 (corresponding to 660 in FIG. 6), where $C_k$ represents a cellularity rank, c represents the cellularity of input image and $p(c>C_k)$ represents the estimated probability of c being greater than $C_k$. Fusing element 770, corresponding to 670 in FIG. 6, operates according to equation 715 to generate a fused cellularity score ĉ. The loss that the neural network model is trained to optimize is defined in equation 725, as a summation of the cross entropies of set of binary classifiers, where $o_k$ is the output probability of the kth binary classifier as defined in equation 705 and $y_k$ is the label of input image for kth binary classifier, in effect a true/false comparison with ground truth. For example, if the cellularity of input image c>Ck, then $y_k$=1 otherwise $y_k$=0. The feedback loops indicated by the dashed lines in FIG. 6 then operate as noted above, to minimize this loss, by adjusting parameters in the fully connected output layer and adjusting parameters of the DCNN model.

There are some very significant differences between the present invention and prior art methods, including those that apply DCNNs to the problem of cellular estimation. One such difference is that the present invention does not require either nuclear segmentation or cell segmentation of the input image patches to be performed. Almost all prior art methods depend on one or both of these as an initial step, in which all the nuclei (or cells) in an image patch are located, classified to distinguish between normal nuclei/cells and cancerous ones, and corresponding areas of interest to be analyzed further are defined. In the present invention, the only sort of segmentation that may optionally occur is a rough sort of tumor segmentation, defining a boundary around the whole tumor area, and removing the surrounding area as a simple background removal step. Avoiding the need for nuclear or cell-based segmentation is a valuable simplification afforded by the present invention.

Another difference is that prior art methods, including those few that avoid a nuclear or cell segmentation step, depend on a type of classification in which a cellularity score—the percentage of cellular area that appears to be taken up by cancer cells—is assigned based on finding the best match in terms of visual appearance to one category "bin" in a pre-established series. For example, if the input image "looks more like" images with ground truth cellularity scores in the range of 20%+/−5% than those images in any other "bins" in the entire 0 to 100% range, the cellularity of that input image will be estimated to be 20%+/−5%. In the present invention, instead of using a DCNN trained by that type of regression model, a direct estimate of a specific cellularity score is provided, from a DCNN trained according to an ordinal regression model.

Systems of the present invention can be realized in the form of stand-alone computer software, or it can be deployed onto the existing clinical CAD (computer-aided diagnosis) systems. Applications for the methods described herein, beyond NAT monitoring and survival prediction, include other image-based rating tasks such as cancer grading.

Although the description has been described with respect to particular embodiments thereof, these particular embodiments are merely illustrative, and not restrictive.

Any suitable programming language can be used to implement the routines of particular embodiments including C, C++, Java, assembly language, etc. Different programming techniques can be employed such as procedural or object oriented. The routines can execute on a single processing device or multiple processors. Although the steps, operations, or computations may be presented in a specific order, this order may be changed in different particular embodiments. In some particular embodiments, multiple steps shown as sequential in this specification can be performed at the same time.

Particular embodiments may be implemented in a computer-readable storage medium for use by or in connection with the instruction execution system, apparatus, system, or device. Particular embodiments can be implemented in the form of control logic in software or hardware or a combination of both. The control logic, when executed by one or more processors, may be operable to perform that which is described in particular embodiments.

Particular embodiments may be implemented by using a programmed general purpose digital computer, by using application specific integrated circuits, programmable logic devices, field programmable gate arrays, optical, chemical, biological, quantum or nanoengineered systems, components and mechanisms may be used. In general, the functions of particular embodiments can be achieved by any means as is known in the art. Distributed, networked systems, components, and/or circuits can be used. Communication, or transfer, of data may be wired, wireless, or by any other means.

It will also be appreciated that one or more of the elements depicted in the drawings/figures can also be implemented in a more separated or integrated manner, or even removed or rendered as inoperable in certain cases, as is useful in accordance with a particular application. It is also within the spirit and scope to implement a program or code that can be stored in a machine-readable medium to permit a computer to perform any of the methods described above.

A "processor" includes any suitable hardware and/or software system, mechanism or component that processes data, signals or other information. A processor can include a system with a general-purpose central processing unit, multiple processing units, dedicated circuitry for achieving functionality, or other systems. Processing need not be limited to a geographic location, or have temporal limitations. For example, a processor can perform its functions in "real time," "offline," in a "batch mode," etc. Portions of processing can be performed at different times and at different locations, by different (or the same) processing systems. Examples of processing systems can include servers, clients, end user devices, routers, switches, networked storage, etc. A computer may be any processor in communication with a memory. The memory may be any suitable processor-readable storage medium, such as random-access memory (RAM), read-only memory (ROM), magnetic or optical disk, or other non-transitory media suitable for storing instructions for execution by the processor.

As used in the description herein and throughout the claims that follow, "a", "an", and "the" includes plural references unless the context clearly dictates otherwise. Also, as used in the description herein and throughout the claims that follow, the meaning of "in" includes "in" and "on" unless the context clearly dictates otherwise.

Thus, while particular embodiments have been described herein, latitudes of modification, various changes, and substitutions are intended in the foregoing disclosures, and it will be appreciated that in some instances some features of particular embodiments will be employed without a corresponding use of other features without departing from the scope and spirit as set forth. Therefore, many modifications may be made to adapt a particular situation or material to the essential scope and spirit.

We claim:

1. A method for automatically estimating cellularity in a digital pathology slide image, the method comprising:

extracting patches of interest from the digital pathology slide image;

operating on each of the extracted patches using a trained first deep convolutional neural network (DCNN) to classify that patch as either normal or suspect, wherein neither cell segmentation nor nuclear segmentation has to be performed for the extraction or for the patch classification by the first DCNN;

using a second DCNN to receive as an input the patches classified as suspect by the first DCNN, and to determine an estimated cellularity score for each suspect patch, the second DCNN having been trained using a deep ordinal regression model which does not include any sorting of images into different categories based on an assessment of whether their cellularity falls into one range or another; and providing as an output the determined cellularity scores of the suspect patches.

2. The method of claim 1, wherein the first and second DCNNs are trained using a first and second plurality of training digital pathology images respectively as inputs.

3. The method of claim 2, wherein each of the first and second pluralities of training digital pathology images is derived at least in part by data augmentation of one or more initial training digital pathology images.

4. The method of claim 3, wherein data augmentation comprises at least one of flipping, rotating and color perturbation.

5. The method of claim 2, wherein training the second DCNN comprises, for each training digital pathology image in the second plurality of training digital pathology images:

a DCNN model extracting image features from the training digital pathology image;

a fully connected output layer operating on the extracted image features to generate a mid-level representation of the training digital pathology image;

a stack of K binary classifiers operating on the mid-level representation, where each binary classifier predicts whether the cellularity of the training digital pathology image is greater than a rank percentage specific to that binary classifier to produce an ordinal output;

fusing the K binary outputs from the stack of binary classifiers at a fusing element that weights the outputs of different classifiers differently to provide a fused cellularity score; and iteratively adjusting parameters of the fully connected output layer and parameters in the DCNN model to minimize a loss function determined by a ground truth cellularity score for the training digital pathology image, such that at loss function minimization, a final trained set of parameters of the fully connected output layer and DCNN model are established for the ordinal regression model.

6. The method of claim 1, further comprising:

combining the estimated cellularity scores of the patches of interest to provide an estimated cellularity for the digital pathology slide image at a patch-by-patch level.

7. The method of claim 1, wherein the digital pathology slide image is a haemotoxylin and eosin (H&E) stained histologic image.

8. The method of claim 6,
wherein the estimated cellularity of the digital pathology slide image is used as a measure of cancer grading.

9. The method of claim 6,
wherein the digital pathology slide image is produced using tissue from a patient; and
wherein the estimated cellularity of the digital pathology slide image is used in a prediction of clinical outcome for the patient.

10. A method of training first and second deep convolutional neural networks to automatically estimate cellularity of digital pathology slide images, the method comprising:
training the first deep convolutional neural network (DCNN) to classify each of a first plurality of training digital pathology images input to the first DCNN as either normal or suspect; and
training the second DCNN to estimate and provide as an output a cellularity score of each of a second plurality of training digital pathology images, using an ordinal regression model, wherein the deep ordinal regression model does not include any sorting of images into different categories based on an assessment of whether their cellularity falls into one range or another.

11. The method of claim 10,
wherein training the second DCNN to estimate an overall cellularity of each of the second plurality of training digital pathology images comprises, for each training digital pathology image:
training a DCNN model to estimate an initial cellularity of the training digital pathology image;
extracting image features from that training digital pathology slide image;
operating on the extracted image features using a fully connected output layer to generate a mid-level representation of the training digital pathology image;
using each of a stack of K binary classifiers to compare the estimated initial cellularity with a threshold rank percentage specific to that binary classifier, to provide a corresponding binary output;
fusing the K binary outputs from the stack of binary classifiers at a fusing element that weights the outputs of different classifiers differently to provide a fused cellularity score; and
iteratively adjusting parameters of the fully connected output layer and parameters in DCNN model to minimize a loss function determined by a ground truth cellularity score for the training digital pathology image, such that at loss function minimization, a final trained set of parameters of the fully connected output layer and DCNN model are established for the ordinal regression model.

12. The method of claim 11,
wherein the loss function includes a summation of cross entropies of the binary classifier outputs.

13. An apparatus for automatically estimating cellularity in a digital pathology slide image, the apparatus comprising:
one or more processors; and
logic encoded in one or more non-transitory media for execution by the one or more processors and when executed operable to:
extract patches of interest from the digital pathology slide image;
operate on each of the extracted patches using a trained first deep convolutional neural network (DCNN) to classify that patch as either normal or suspect
operate on each of the suspect patches using a second DCNN to receive as an input the patches classified as suspect by the first DCNN, and to determine an estimated cellularity score for each suspect patch, the second DCNN having been trained using a deep ordinal regression model which does not include any sorting of patches into different categories based on an assessment of whether their cellularity falls into one range or another; and
provide as an output the determined cellularity scores of the suspect patches.

14. The apparatus of claim 13,
wherein the first and second DCNNs are trained using a first and second plurality of training digital pathology images respectively as inputs.

15. The apparatus of claim 14,
wherein each of the first and second pluralities of training digital pathology images is derived at least in part by data augmentation of one or more initial training digital pathology images.

16. The apparatus of claim 15,
wherein data augmentation comprises at least one of flipping, rotating and color perturbation.

17. The apparatus of claim 15,
wherein neither nuclear segmentation nor cell segmentation is required for successful operation of the method.

18. The apparatus of claim 13,
wherein the digital pathology slide image is a haemotoxylin and eosin (H&E) stained histologic image.

19. The apparatus of claim 13,
wherein the estimated cellularity of the digital pathology slide image is used as a measure of cancer grading.

20. The apparatus of claim 14,
wherein training the second DCNN comprises, for each training digital pathology image in the second plurality of training digital pathology images:
a DCNN model extracting image features from the training digital pathology image;
a fully connected output layer operating on the extracted image features to generate a mid-level representation of the training digital pathology image;
a stack of K binary classifiers operating on the mid-level representation, where each binary classifier predicts whether the cellularity of the training digital pathology image is greater than a rank percentage specific to that binary classifier to produce an ordinal output;
fusing the K binary outputs from the stack of binary classifiers at a fusing element that weights the outputs of different classifiers differently to provide a fused cellularity score; and
iteratively adjusting parameters of the fully connected output layer and parameters in the DCNN model to minimize a loss function determined by a ground truth cellularity score for the training digital pathology image, such that at loss function minimization, a final trained set of parameters of the fully connected output layer and DCNN model are established for the ordinal regression model.

* * * * *